US008337527B2

(12) United States Patent
Hawkins et al.

(10) Patent No.: US 8,337,527 B2
(45) Date of Patent: Dec. 25, 2012

(54) SPINAL CONNECTOR (75) Inventors: Nathaniel E. Hawkins, Greensboro, NC (US); Nicholas J. Bender, Lake Hiawatha, NJ (US); Rui J. Ferreira, Livingston, NJ (US)

(73) Assignee: EBI, LLC, Parsippany, NJ (US)

( * ) Notice: Subject to any disclaimer, the term of this patent is extended or adjusted under 35 U.S.C. 154(b) by 988 days.

(21) Appl. No.: 12/099,227

(22) Filed: Apr. 8, 2008

(65) Prior Publication Data
US 2008/0262553 A1  Oct. 23, 2008

Related U.S. Application Data (60) Provisional application No. 60/912,493, filed on Apr. 18, 2007.

(51) Int. Cl.
*A61B 17/70* (2006.01)
(52) U.S. Cl. .......................... 606/278; 606/151
(58) Field of Classification Search .............. 606/151, 606/246–278, 60; *A61B 17/08, 17/58*
See application file for complete search history.

(56) References Cited

U.S. PATENT DOCUMENTS

| 5,133,717 | A | 7/1992 | Chopin et al. |
| 5,910,142 | A | 6/1999 | Tatar |
| 5,993,449 | A | 11/1999 | Schlapfer et al. |
| 6,749,612 | B1 | 6/2004 | Conchy et al. |
| 6,960,212 | B2 | 11/2005 | Richelsoph et al. |
| 7,175,522 | B2 | 2/2007 | Hartl |
| 7,575,587 | B2 * | 8/2009 | Rezach et al. ............... 606/278 |
| 2003/0032959 | A1 * | 2/2003 | Yeh ............................. 606/61 |
| 2003/0229345 | A1 * | 12/2003 | Stahurski .................... 606/61 |
| 2005/0154388 | A1 | 7/2005 | Roussouly et al. |
| 2005/0192572 | A1 * | 9/2005 | Abdelgany et al. ......... 606/61 |
| 2005/0228378 | A1 * | 10/2005 | Kalfas et al. ............... 606/61 |
| 2005/0277928 | A1 | 12/2005 | Boschert |
| 2005/0277932 | A1 * | 12/2005 | Farris ......................... 606/61 |
| 2006/0089644 | A1 * | 4/2006 | Felix .......................... 606/61 |
| 2006/0247626 | A1 * | 11/2006 | Taylor et al. ............... 606/61 |

FOREIGN PATENT DOCUMENTS
WO  WO-2005099603  10/2005

OTHER PUBLICATIONS

Extended European Search Report on European Patent Application No. EP 08 15 4821 mailed Feb. 27, 2008.

* cited by examiner

*Primary Examiner* — Alvin Stewart
*Assistant Examiner* — James Palmer
(74) *Attorney, Agent, or Firm* — Harness, Dickey (57) ABSTRACT

A spinal connector includes a first seat having a first opening for coupling to a first spinal connecting member along a first longitudinal axis and a second seat having a second opening for coupling to a second spinal connecting member along a second longitudinal axis. The second longitudinal axis is substantially coaxial to the first longitudinal axis for connecting the first and second connecting members end to end. The spinal connector also includes a ball enclosure rotatably received in the second opening of the second seat. The ball enclosure defines a bore along the second longitudinal axis and articulates with the second opening for allowing change of orientation of the second connecting member relative to the first connecting member.

24 Claims, 10 Drawing Sheets

SPINAL CONNECTOR

CROSS-REFERENCE TO RELATED APPLICATIONS

This application claims the benefit of U.S. Provisional Application No. 60/912,493, filed Apr. 18, 2007. The disclosure of the above application is incorporated herein by reference.

INTRODUCTION

Various spinal devices are known for coupling two spinal connecting members for spinal stabilization, fusion or other spinal procedures.

The present teachings provide a spinal connector that can accommodate two or more spinal connecting members of various sizes and/or in variable orientations relative to each other.

SUMMARY

The present teachings provide a spinal connector that can connect two or more connecting members for the spine in side-by-side or end-to-end arrangements or in combinations thereof. The spinal connector can include a seat having a coupling element that allows polyaxial support for the corresponding connecting member.

In one aspect, the spinal connector includes a first seat having a first opening for coupling to a first spinal connecting member along a first longitudinal axis and a second seat having a second opening for coupling to a second spinal connecting member along a second longitudinal axis, the second longitudinal axis substantially coaxial to the first longitudinal axis for connecting the first and second connecting members end to end. The spinal connector also includes a ball enclosure rotatably received in the second opening of the second seat. The ball enclosure defines a bore along the second longitudinal axis and articulates with the second opening for allowing change of orientation of the second connecting member relative to the first connecting member.

In another aspect, the spinal connector includes at least first, second and third seats corresponding to first, second and third side-by-side openings for coupling to corresponding first, second and third elongated spinal connecting members side by side. The spinal connector also includes at least one ball enclosure rotatable received in at least one of the first, second or third seats for changing a longitudinal orientation of the corresponding connecting member relative to the other connecting members.

In a further aspect, the spinal connector includes a body defining at least first and second seats. The first seat includes a substantially V-shaped lower surface defining a first longitudinal opening along a first longitudinal axis for receiving a first spinal connecting member, and an inner upper surface defined by first and second opposing arms. The second seat includes a substantially spherical lower surface rotatably receiving a ball enclosure having a longitudinal bore, the longitudinal bore defining a second longitudinal axis for receiving a second spinal connecting member at a variable orientation relative to the first connecting member. The second seat also includes a peripheral wall defining a circular inner upper opening. The spinal connector also includes a first locking element threadably engageable to the first and second arms of the first seat for securing the first connecting member to the first seat, and a second locking element threadably received in the circular upper opening of the second seat for securing the second connecting member to the second seat.

In yet another aspect the present teachings provide a spinal connector device that includes a first spinal connecting member, a second spinal connecting member, and a body defining at least first and second seats. The first seat includes a first substantially V-shaped lower surface defining a first longitudinal opening along a first longitudinal axis receiving the first spinal connecting member. The first seat engages the first connecting member in line contact. The second seat includes a second substantially V-shaped lower surface defining a second longitudinal opening along a second longitudinal axis for receiving the second spinal connecting member. The second seat engages the second connecting member in line contact.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is in no way intended to limit the invention, its application, or uses.

Figure 1:
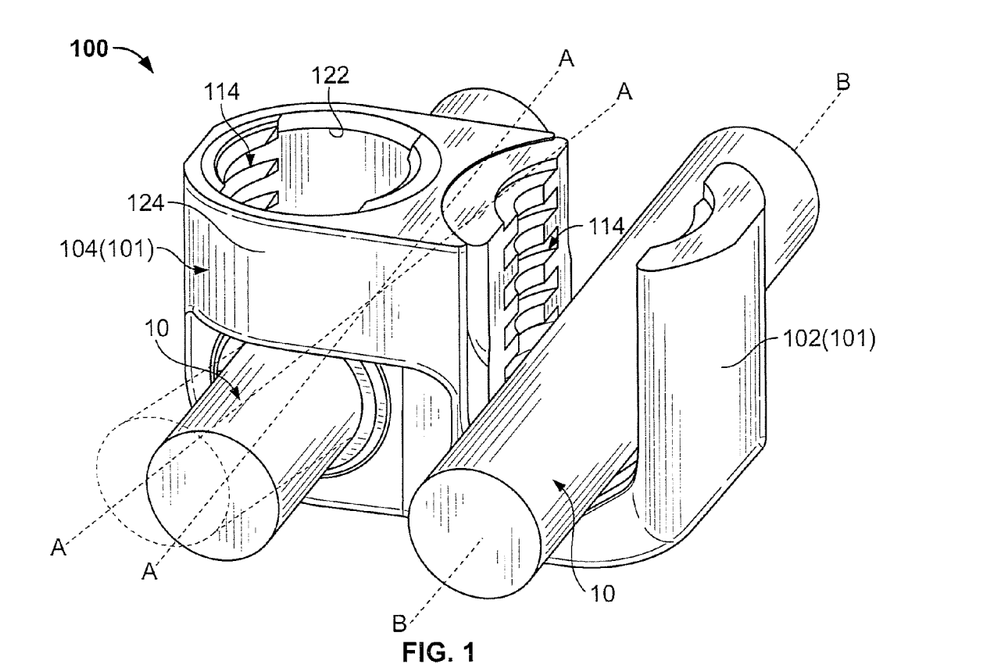
FIG. 1 is a perspective view of a spinal connector according to the present teachings, the spinal connector shown associated with two spinal connecting members.
Figures 6, 7:
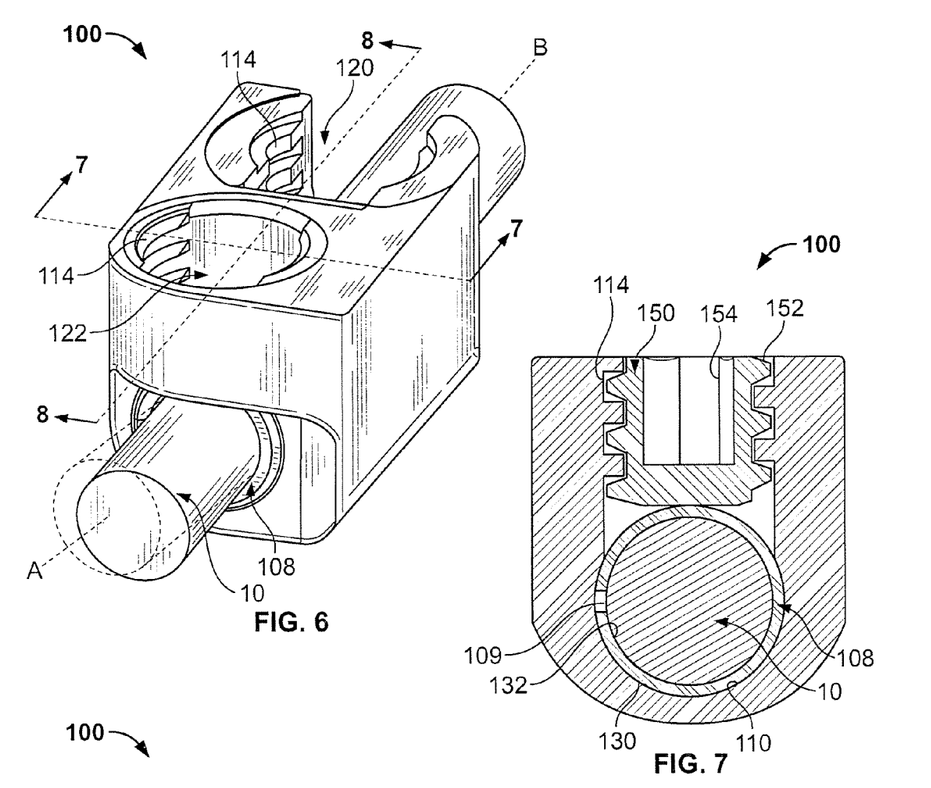
FIG. 6 is a perspective view of a spinal connector according to the present teachings, the spinal connector shown associated with two spinal connecting members.
FIG. 7 is a sectional view of the spinal connector of FIG. 6, taken along line 7-7 of FIG. 6, the spinal connector shown associated with a locking element.
Figure 11:
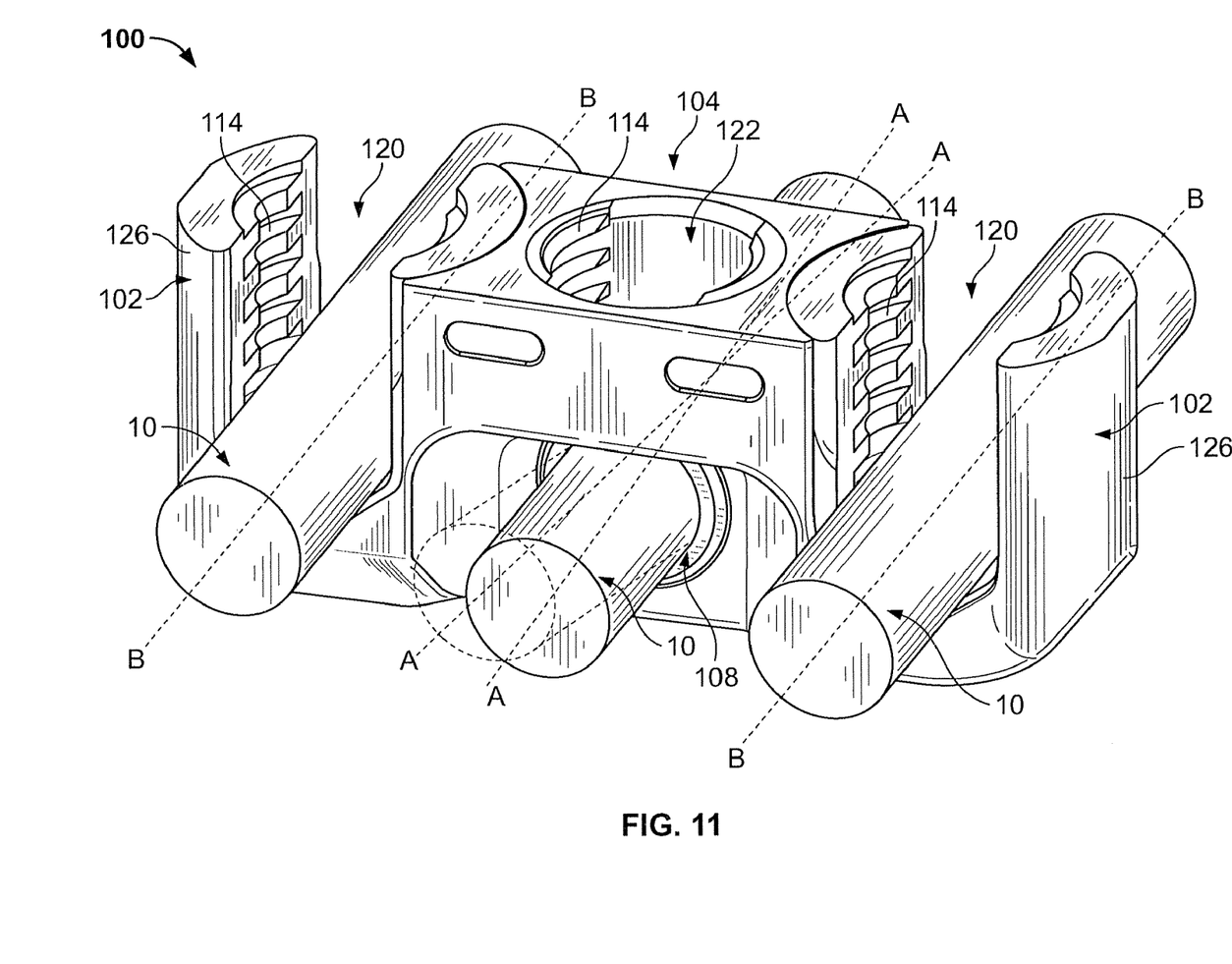
FIG. 11 is a perspective view of a spinal connector according to the present teachings, the spinal connector shown associated with three spinal connecting members.
Figure 12:
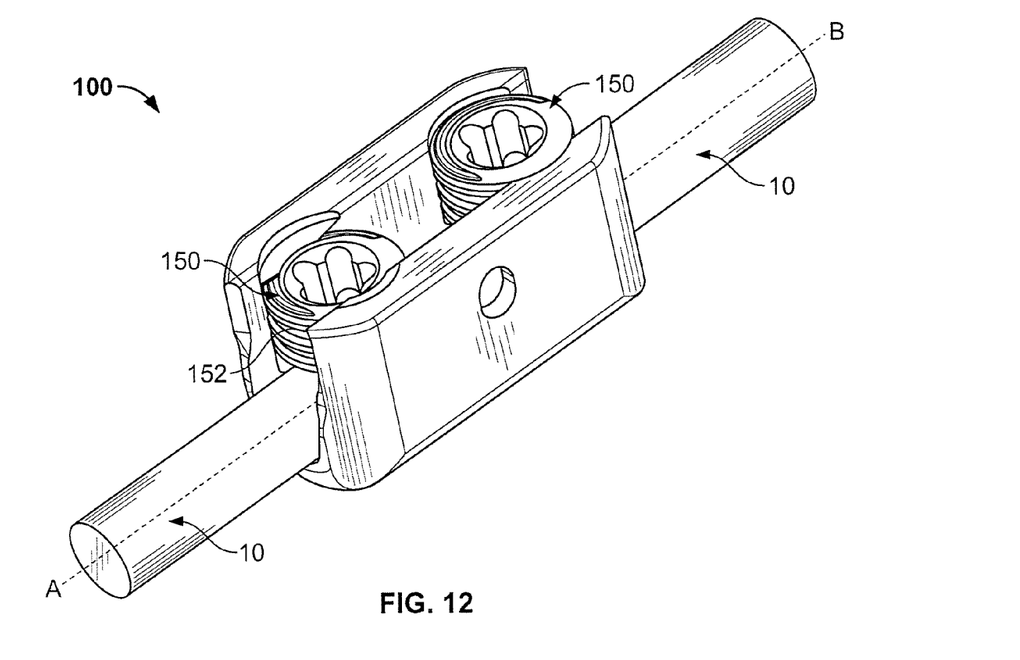
FIG. 12 is a perspective view of a spinal connector according to the present teachings, the spinal connector shown associated with two spinal connecting members.
Figure 13:
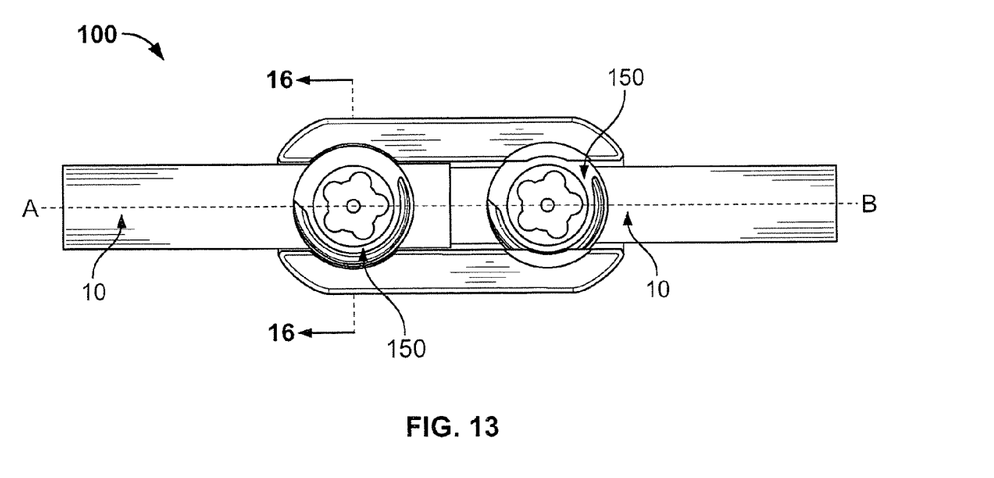
FIG. 13 is a top view of the spinal connector of FIG. 12.
Figure 14:
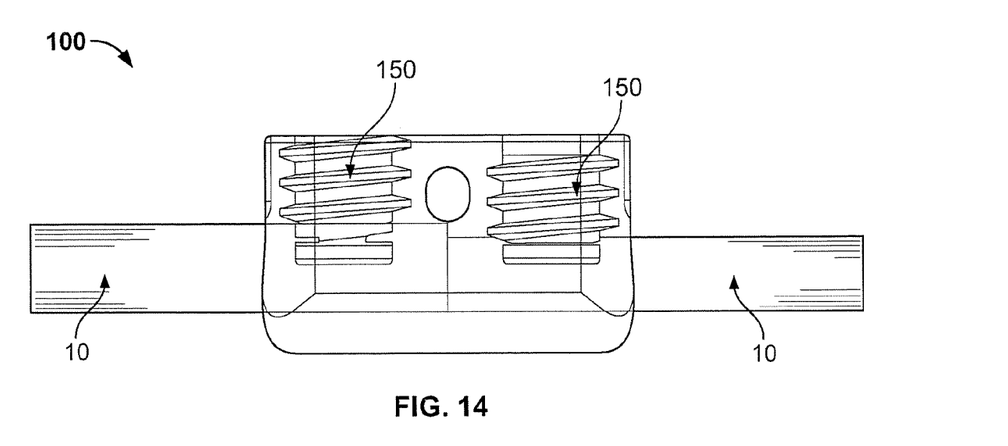
FIG. 14 is a side view of the spinal connector of FIG. 12.
Figure 15:
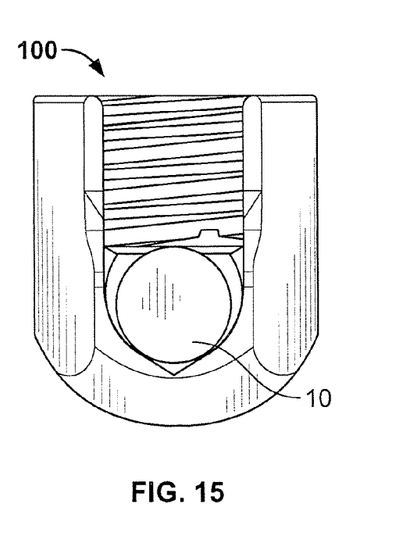
FIG. 15 is an end view of the spinal connector of FIG. 12.
Figure 16:
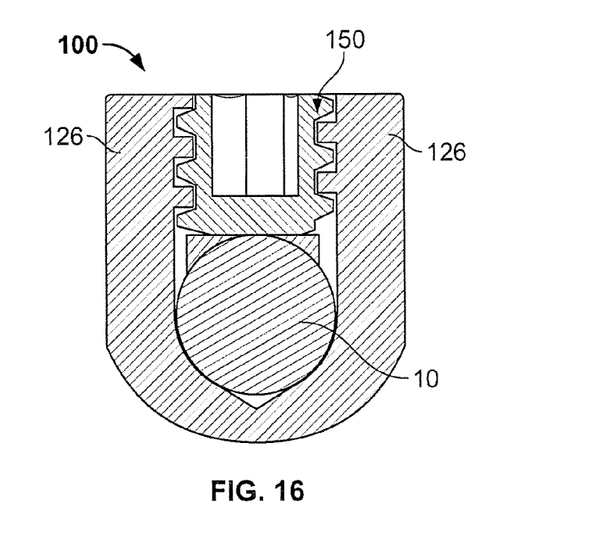
FIG. 16 is a sectional view of the spinal connector of FIG. 12, taken along line 16-16 of FIG. 13.
Figure 17:
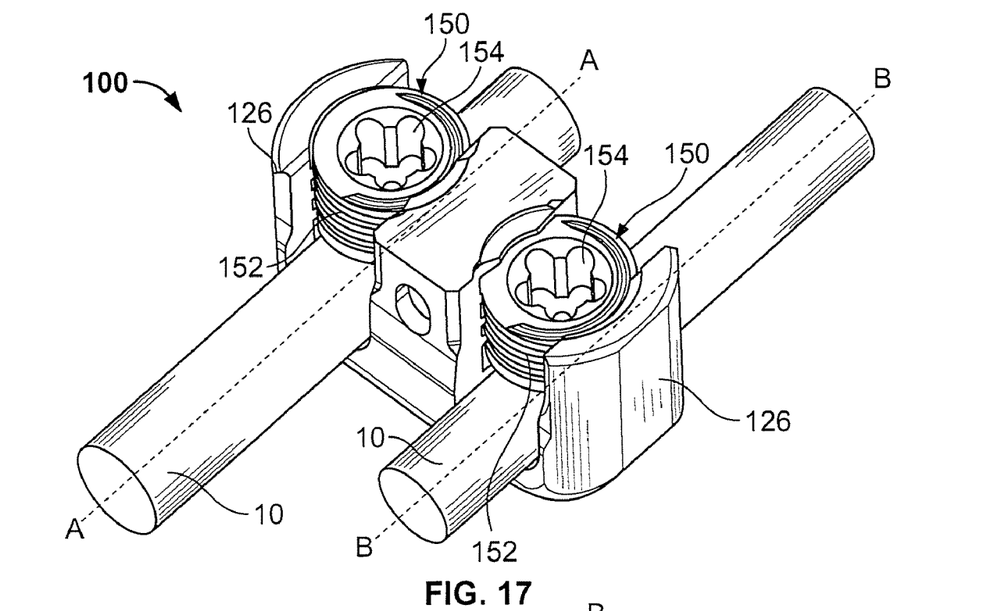
FIG. 17 is a perspective view of a spinal connector according to the present teachings, the spinal connector shown associated with two spinal connecting members.
Figure 18:
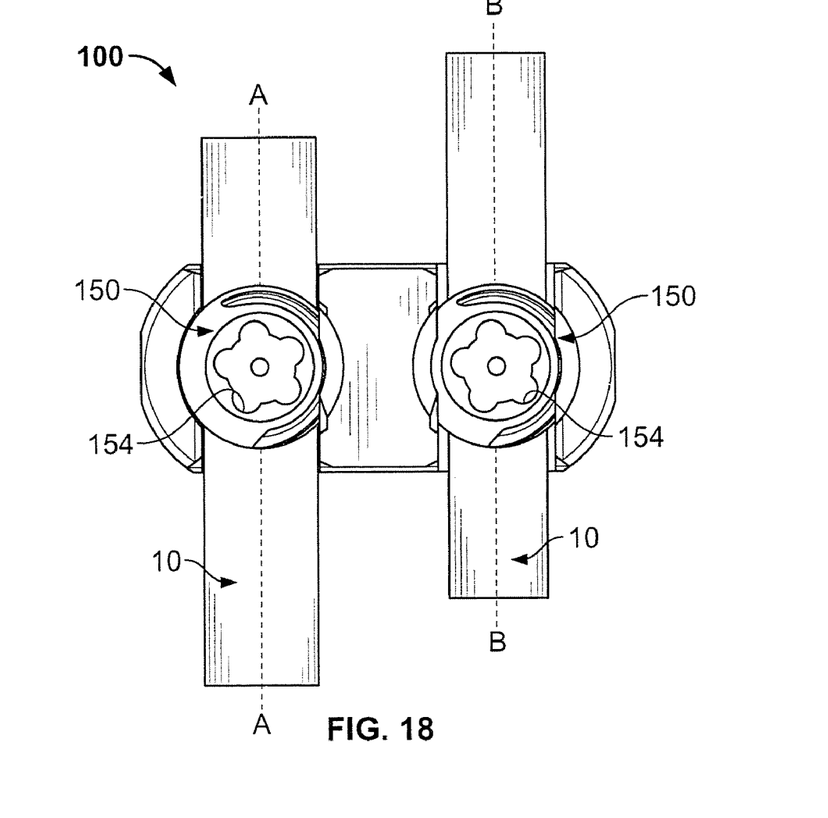
FIG. 18 is a top view of the spinal connector of FIG. 17.
Figure 19:
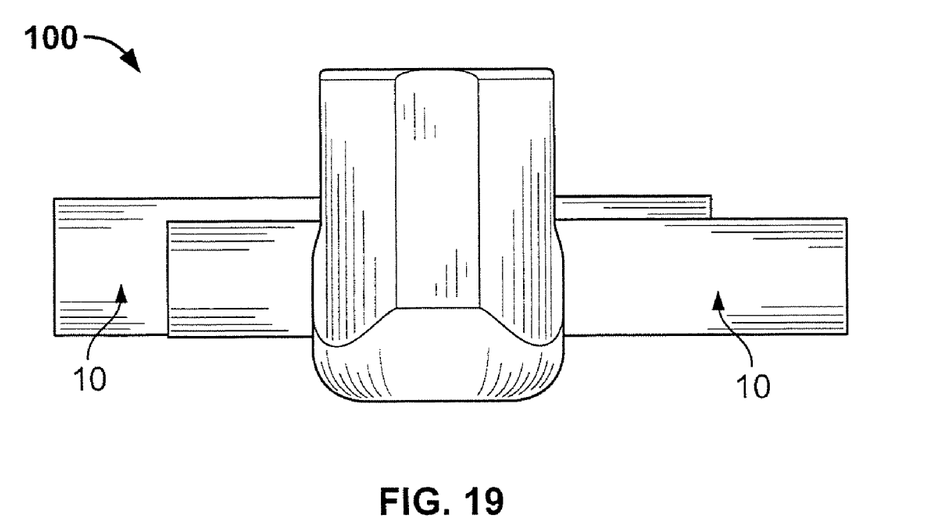
FIG. 19 is an end view of the spinal connector of FIG. 17.

The present teachings provide a spinal connector 100 that can be used to interconnect two or more elongated spinal connecting members 10, such as connecting rods for the spine, for example. The spinal connecting members 10 can have circular, or oval or elliptical or polygonal or otherwise shaped cross-sections with different diameters or widths. The spinal connector 100 can connect two or more connecting members 10 side by side or next to each other, as illustrated in FIGS. 1, 11 and 17, for example. The spinal connector 100 can also be used to connect two connecting members 10 end to end, as illustrated in FIGS. 6 and 12, for example. The spinal connector 100 can also be used to connect three or more connecting members 10 side by side, as illustrated in FIG. 11 for three connecting members 10.

Although not specifically illustrated, the spinal connector 100 can also connect at least three connecting members 10 in a combination of side by side and end to end orientations. For example, the spinal connector 100 of FIG. 1 can be combined with the spinal connector 100 of FIG. 6 or with the spinal connector 100 of FIG. 12 to provide a spinal connector 100 that includes first and second connecting members 10 arranged end to end, and at least one other (third) connecting member 10 arranged side by side relative to the first and second connecting members 10. It will be appreciated that the spinal connectors 100 illustrated herein are only representative of the present teachings. Various features of the spinal connectors 100 illustrated in FIGS. 1-20 can be selectively combined to provide different spinal connectors 100 for connecting two or more connecting members 10 in various spatial relationships to each other, including side by side, end to end, and combinations thereof, as well as with different and/or variable and polyaxial orientations relative to each other.

Referring to FIGS. 1-5, and 17-20 exemplary spinal connectors 100 according to the present teachings can be used to connect first and second connecting members 10 side by side. Referring particularly to FIGS. 1-5, the spinal connector 100 can provide polyaxial support for at least one of the connecting members 10, such that the relative orientation of the connecting members 10 can vary, as illustrated in FIG. 1. Specifically, the first connecting member 10 can be oriented along a first longitudinal axis A that can have variable orientation relative the fixed orientation of the second connecting member 10, which is oriented along a fixed longitudinal axis B. It will be appreciated that the spinal connector 100 can also provide polyaxial support for both the first and second connecting members 10.

Alternatively, the spinal connector 100 can provide a fixed orientation of the respective first and second axes A and B of the first and second connecting members 10 in a side by side configuration, as illustrated in FIG. 17. Although the connecting members 10 are shown as being substantially parallel, it will be appreciated that the spinal connector 100 can support the connecting members 10 at other fixed angles defined by a fixed angle between the axes A and B.

Referring to FIGS. 6-10 and 12-16, exemplary spinal connectors 100 according to the present teachings can be used to connect first and second connecting members 10 in end to end configurations. Referring particularly to FIGS. 6-10, the spinal connector 100 can provide polyaxial support for at least one of the first and second connecting members 10, such that the relative orientation of the first and second longitudinal axes A and B of the respective first and second connecting members 10 can vary, as illustrated in FIG. 6. It will be appreciated that the spinal connector 100 can also provide polyaxial support for both the first and second connecting members 10.

Alternatively, the spinal connector 100 can provide a fixed orientation of the respective first and second axes A and B of the first and second connecting members 10 in an end to end configuration, as illustrated in FIG. 12. Although the connecting members 10 are shown as being substantially coaxial, it will be appreciated that the spinal connector 100 can be angled such that the spinal connector 100 can support the connecting members 10 at other fixed angles defined by a fixed angle between the axes A and B.

Referring to FIG. 11, an exemplary spinal connector 100 for connecting three connecting members 10 is illustrated. Although the spinal connector 100, as illustrated in FIG. 11, is symmetric and provides support along fixed axes B for two end connecting members 10 and polyaxial support along variable axis A for the center connecting member 10, it will be appreciated that all other possible combinations of supporting three connecting members 10 are within the scope of the present teachings. For example, the spinal connector 100 of FIG. 11 can be either non-symmetric or symmetric. Further, the spinal connector 100 can provide polyaxial support for the center connecting member 10 and only one of the two end connecting members 10, or provide polyaxial support of only one of the end connecting members 10, or provide polyaxial support for both end connecting members 10, but not for the center connecting member 10. Further, it will be appreciated that other connecting members 10 can be supported either in side by side or end to end configurations relative to the existing connecting members 10, as discussed above.

Referring generally to FIGS. 1-20, various features that can be included in any of the above-mentioned aspects of the spinal connector 100 are described. Although specific figures are referenced for illustration, it will be appreciated that similar features referenced with similar reference numerals may also be present in other aspects or configurations of the spinal connector 100 and shown in other figures. Generally, the spinal connector 100 can include two or more seats 101 for supporting a corresponding number of connecting members 10, as illustrated, for example in FIG. 1. Each seat 101 can be of the fixed orientation type 102 or the polyaxial orientation type 104.

Figure 2:
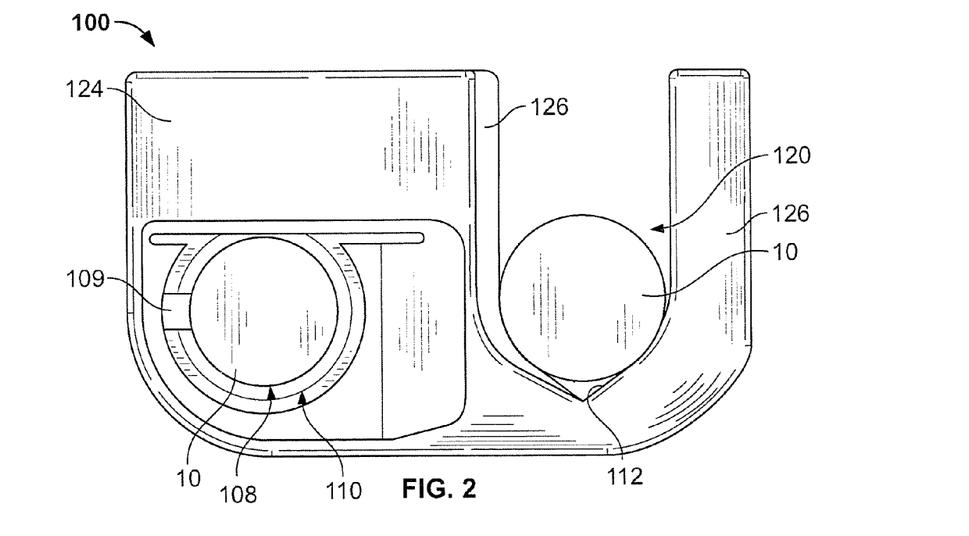
FIG. 2 is a side view of the spinal connector of FIG. 1.
Figure 3:
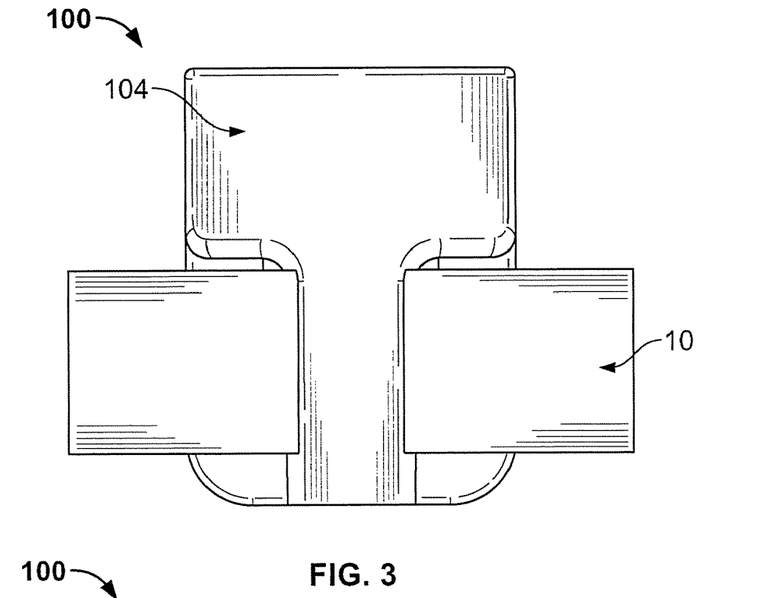
FIG. 3 is an end view of the spinal connector of FIG. 1.
Figure 4:
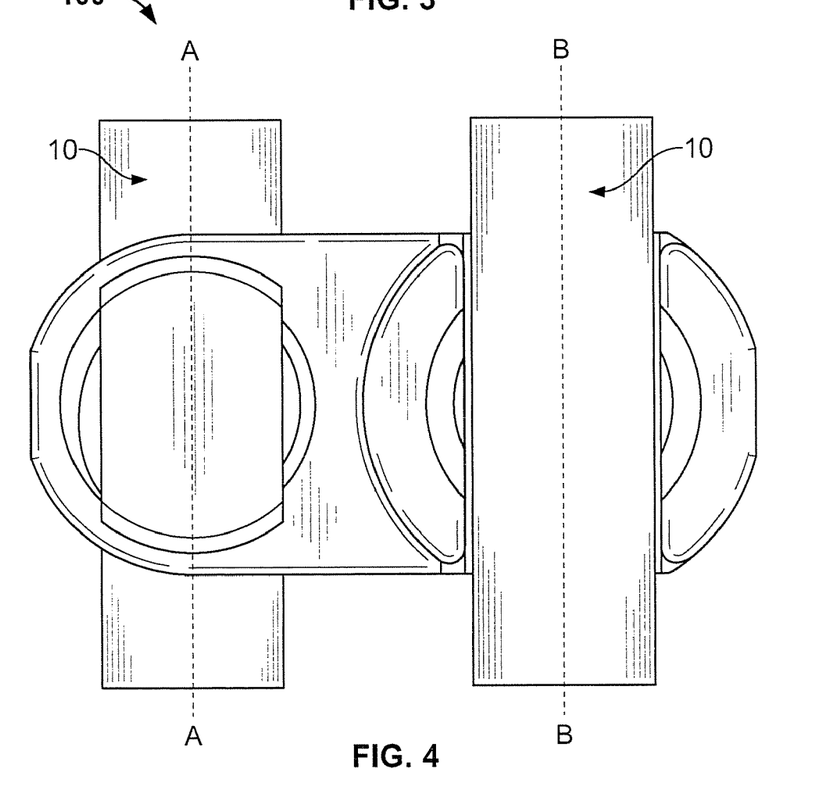
FIG. 4 is a top view of the spinal connector of FIG. 1.
Figure 5:
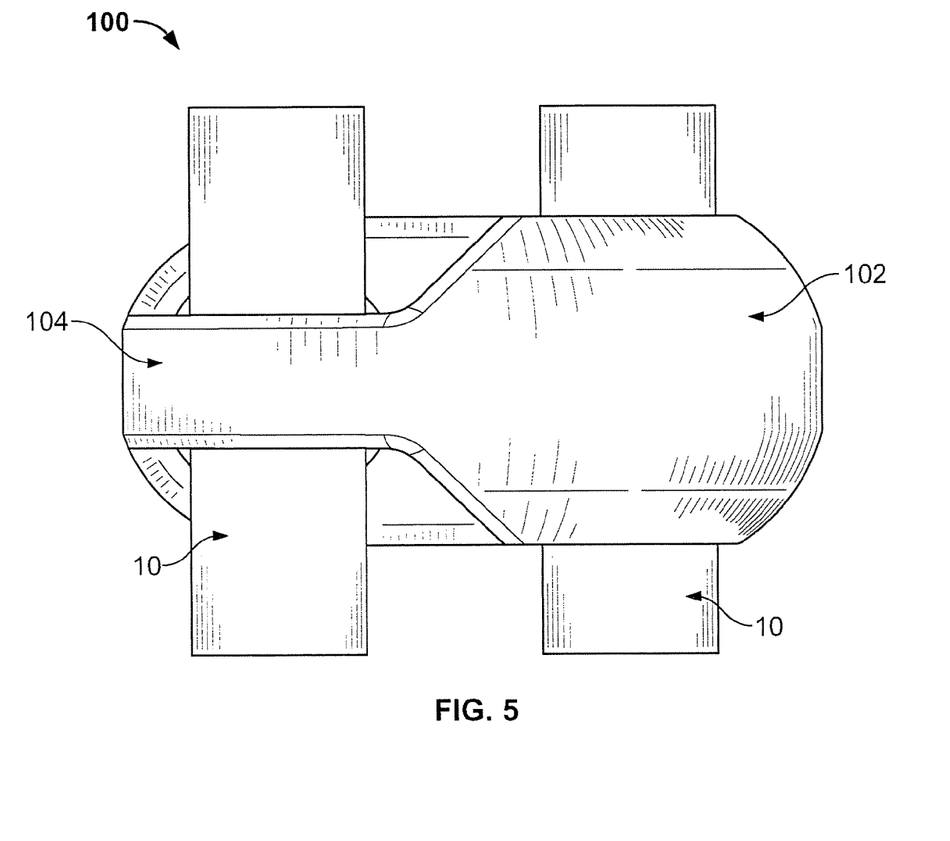
FIG. 5 is a bottom view of the spinal connector of FIG. 1.

The seat of the fixed orientation type or fixed-support seat 102 can support a connecting member 10 along axis B having a fixed orientation relative to the spinal connector 100. The fixed-support seat 102 can include a substantially V-shaped bottom surface 112 that can provide multiple-point contact with the corresponding connecting member 10 along straight contact lines, as shown in FIG. 2, for example. Alternatively, the bottom surface 112 of the fixed-support seat 102 can be substantially U-shaped and substantially conform to a portion of the outer cylindrical surface of the connecting member 10. The fixed-support seat 102 can be saddle-shaped having two upright arms 126 that define an opening 120 for receiving a corresponding connecting member 10. The arms 126 can include engagement formations 114 for engaging a locking element 150, such as a set screw, for example, that can be used to secure the connecting member 10 on the seat 101, as shown in FIGS. 7, 12 and 17, for example. The locking element 150 can include corresponding engagement formations 152 that can mate with the engagement formations 114 of the corresponding seat 101. The engagement formations 114 can be provided in any of various thread designs, including, for example, helical flange, buttress thread, reverse buttress thread and standard thread. The open configuration of the fixed-support seat 102 allows the connecting member 10 to be received in the fixed-support seat either before or after the connecting member 10 is already locked between two pedicle screws.

Figure 8:
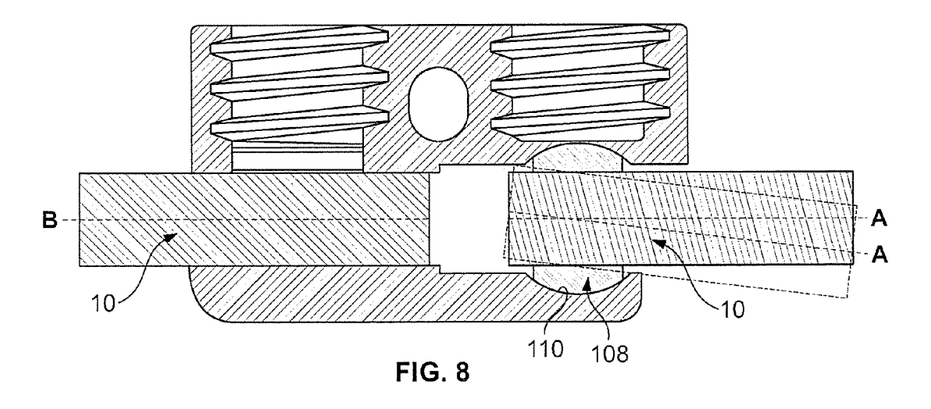
FIG. 8 is a sectional view of the spinal connector of FIG. 6, taken along line 8-8 of FIG. 6.
Figure 9:
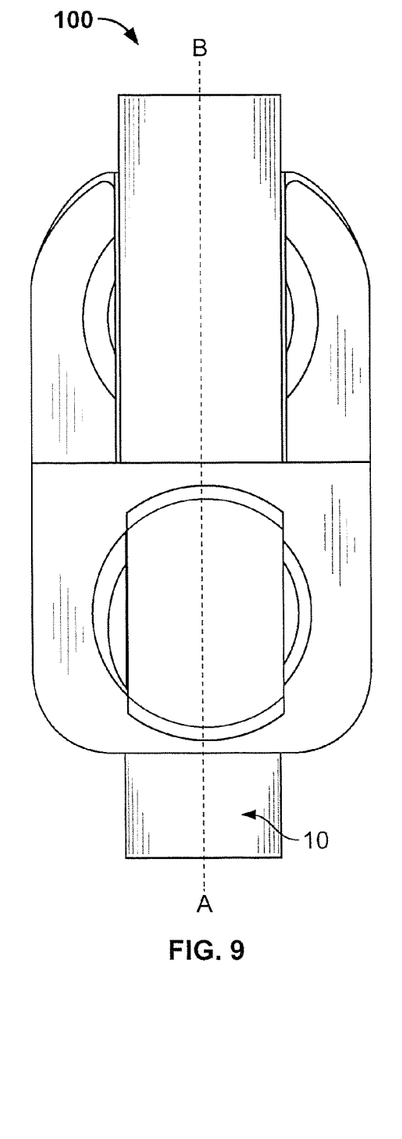
FIG. 9 is a top view of the spinal connector of FIG. 6.
Figure 10:
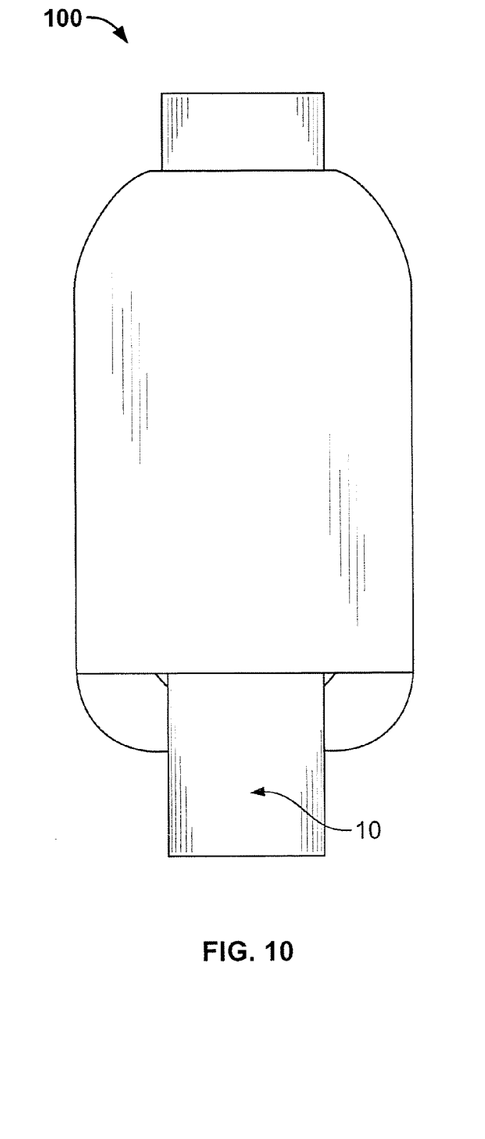
FIG. 10 is a bottom view of the spinal connector of FIG. 6.

The polyaxial support seat 104 can include a substantially spherically shaped bottom surface 110 that can receive a coupling element 108 in the form of a ball enclosure having an outer spherical surface 130 mateable with the bottom surface 110 for polyaxial articulation therebetween, as shown, for example, in FIGS. 6-8. The coupling element 108 can have an inner bore 132 of substantially cylindrical shape that substantially matches the cross-sectional shape of the connecting member 10, as shown in FIG. 7. The connecting member 10 can be slidably received in the bore 132. The coupling element 108 can include one or more slits 109 that can contribute to the resiliency of the coupling element 108 for better clamping on the connecting member 10. The polyaxial seat 104 can include an upper peripheral wall 124 defining an upper opening 122, which can be peripherally fully enclosed, such that the connecting member 10 can be loaded in the polyaxial seat 104 from the end of the connecting member 10. The upper opening 122 of the polyaxial seat 104 can include engagement formations 114 mateable with a corresponding locking element 150. The locking element 150 can include a blind driver bore 154 for receiving a driver (not shown). The locking element 150 can be driven along the bore 122 of the polyaxial seat 104 for pressing on the coupling element 108 and securing the corresponding connecting member 10.

Figure 20:
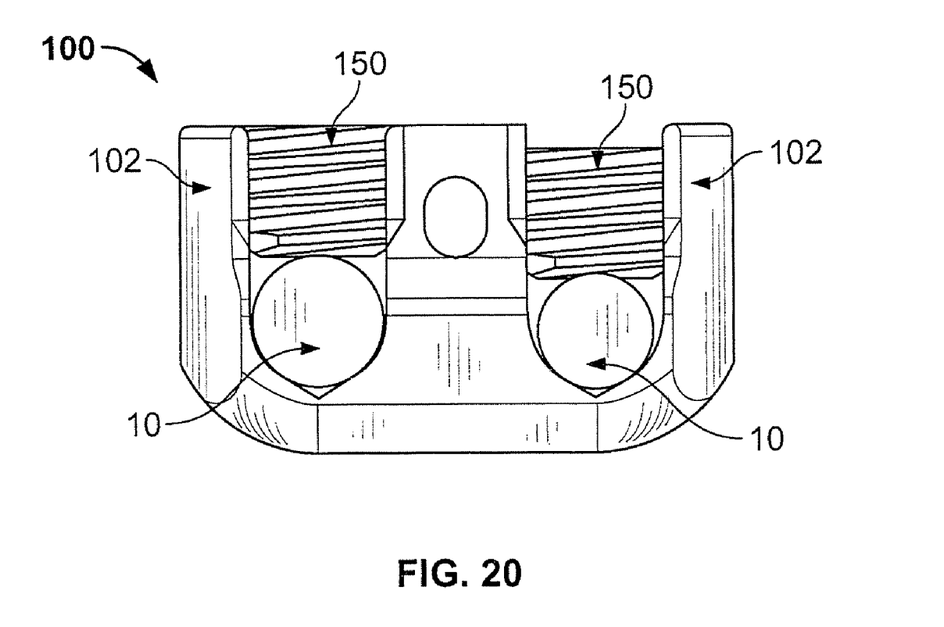
FIG. 20 is a side view of the spinal connector of FIG. 17.

In each aspect described above, the spinal connector 100 can include two or more seats 101 that have different cross-sectional sizes or widths and can accommodate connecting members 10 having different cross-sectional diameter or size or widths, as shown, for example, in FIG. 20 for two seats 101 of the fixed-support type 102, although all the spinal connectors 100, including those shown in FIGS. 1, 6, 11, and 12 can include seats 101 for different size connecting members 10.

In another aspect, the spinal connector 100 can include at least two seats 101 of the fixed-support type 102, each with a substantially V-shaped bottom surface 112 for coupling corresponding connecting members 10 in fixed orientations relative to one another side by side, or end to end, or in combinations thereof.

The spinal connectors 100 can be made of any biocompatible materials, including metals, such as titanium, alloys or polymeric materials. Similarly, the connecting members 10 can be made of various materials, including for example, PEEK, titanium, stainless steel and other biocompatible materials, or combinations thereof.

The foregoing discussion discloses and describes merely exemplary arrangements of the present teachings. One skilled in the art will readily recognize from such discussion, and from the accompanying drawings and claims, that various changes, modifications and variations can be made therein without departing from the spirit and scope of the present teachings.

What is claimed is:

1. A spinal connector comprising:

a body defining first, second and third seats orientated in a side-by-side configuration;

the first and second seats each having a lower surface and inner and outer opposed arms extending upwardly from the lower surface and defining respective first and second longitudinal openings having first and second longitudinal axes adapted to receive respective first and second spinal connecting members therein, the outer arms defining opposed lateral ends of the spinal connector;

the third seat having opposed lateral sides defining the inner arms of the first and second seats, an upper peripheral wall defining a third circular opening and a substantially spherically shaped lower surface rotatably receiving a ball enclosure, the ball enclosure having a spherically shaped outer surface and a longitudinal through-bore defining a third longitudinal axis adapted to receive a third spinal connecting member at a variable orientation relative to the first and second connecting members; and first, second and third locking elements threadably engageable with the corresponding first, second and third openings for securing the respective first, second and third spinal connecting members to the corresponding first, second and third seats, the third locking element configured to engage the ball enclosure.

2. The spinal connector of claim 1, wherein the ball enclosure is resilient.

3. The spinal connector of claim 1, wherein the lower surface of the first and second seats is substantially V-shaped.

4. The spinal connector of claim 1, wherein the first and second longitudinal axes are parallel to each other.

5. The spinal connector of claim 1, wherein the circular opening of the third seat is fully peripherally enclosed by the upper peripheral wall.

6. The spinal connector of claim 1, wherein at least one of the first and second longitudinal openings and the longitudinal through-bore have different widths.

7. The spinal connector of claim 1, wherein the ball enclosure includes at least one through-slit.

8. The spinal connector of claim 1, wherein the lower surface of the first and second seats is substantially U-shaped.

9. The spinal connector of claim 1, wherein the third seat is positioned between the first and second seats.

10. The spinal connector of claim 1, wherein the first, second and third longitudinal axes are in the same plane.

11. A spinal connector comprising:

a body defining first, second and third seats orientated in a side-by-side configuration;

the first and second seats each having a lower surface and inner and outer opposed arms extending upwardly from the lower surface and defining respective first and second longitudinal openings having first and second longitudinal axes adapted to receive respective first and second spinal connecting members therein, the outer arms defining opposed lateral ends of the spinal connector;

the third seat having opposed lateral sides defining the inner arms of the first and second seats, an upper peripheral wall defining a third circular opening and a substantially spherically shaped lower surface rotatably receiving a resilient ball enclosure, the ball enclosure having a spherically shaped outer surface and a longitudinal through-bore defining a third longitudinal axis adapted to receive a third spinal connecting member at a variable orientation relative to the first and second connecting members, the first and second longitudinal axes being parallel to each other; and first, second and third locking elements threadably engageable with the corresponding first, second and third openings for securing the respective first, second and third spinal connecting members to the corresponding first, second and third seats, the third locking element configured to engage the ball enclosure to secure the third connecting member in the third seat.

12. The spinal connector of claim 11, wherein the ball enclosure includes at least one through-slit.

13. The spinal connector of claim 11, wherein at least one of the first and second longitudinal openings and the longitudinal through-bore have different widths.

14. The spinal connector of claim 11, wherein the lower surface of the first and second seats is substantially V-shaped.

15. The spinal connector of claim 11, wherein the lower surface of the first and second seats is substantially U-shaped.

16. The spinal connector of claim 11, wherein the circular opening of the third seat is fully peripherally enclosed by the upper peripheral wall.

17. The spinal connector of claim 11, wherein the third seat is positioned between the first and second seats.

18. The spinal connector of claim 11, wherein the first, second and third longitudinal axes are in the same plane.

19. A spinal connector comprising:
- a body defining first, second and third seats orientated in a side-by-side configuration with the third seat being positioned between the first and second seats;
- the first and second seats each having a lower surface and inner and outer opposed arms extending upwardly from the lower surface and defining respective first and second longitudinal openings having first and second longitudinal axes adapted to receive respective first and second spinal connecting members therein, the outer arms defining opposed lateral ends of the spinal connector;
- the third seat having opposed lateral sides defining the inner arms of the first and second seats, an upper peripheral wall defining a third circular opening and a substantially spherically shaped lower surface rotatably receiving a resilient ball enclosure, the ball enclosure having a spherically shaped outer surface and a longitudinal through-bore defining a third longitudinal axis adapted to receive a third spinal connecting member at a variable orientation relative to the first and second connecting members and the body; and
- first, second and third locking elements threadably engageable with the corresponding first, second and third openings for securing the respective first, second and third spinal connecting members to the corresponding first, second and third seats, the third locking element configured to engage the ball enclosure to secure the third connecting member in the third seat;
- wherein at least one of the first and second longitudinal openings and the longitudinal through-bore have different widths.

20. The spinal connector of claim 16, wherein the lower surface of the first and second seats is substantially V-shaped.

21. The spinal connector of claim 16, wherein the ball enclosure includes at least one through-slit.

22. The spinal connector of claim 16, wherein the lower surface of the first and second seats is substantially U-shaped.

23. The spinal connector of claim 16, wherein the circular opening of the third seat is fully peripherally enclosed by the upper peripheral wall.

24. The spinal connector of claim 19, wherein the first, second and third longitudinal axes are in the same plane and the first and second longitudinal axes are parallel to each other.

* * * * *

UNITED STATES PATENT AND TRADEMARK OFFICE
CERTIFICATE OF CORRECTION

| | |
|---|---|
| PATENT NO. | : 8,337,527 B2 |
| APPLICATION NO. | : 12/099227 |
| DATED | : December 25, 2012 |
| INVENTOR(S) | : Nathaniel E. Hawkins et al. |

Page 1 of 1

It is certified that error appears in the above-identified patent and that said Letters Patent is hereby corrected as shown below:

In the Claims:

Column 8, Line 15:     "claim 16" should be --claim 19--

Column 8, Line 17:     "claim 16" should be --claim 19--

Column 8, Line 19:     "claim 16" should be --claim 19--

Column 8, Line 21:     "claim 16" should be --claim 19--

Signed and Sealed this
Tenth Day of September, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,337,527 B2 | Page 1 of 1 |
| APPLICATION NO. | : 12/099227 | |
| DATED | : December 25, 2012 | |
| INVENTOR(S) | : Hawkins et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1120 days.

Signed and Sealed this
Thirtieth Day of December, 2014

Michelle K. Lee
*Deputy Director of the United States Patent and Trademark Office*